US00PP25658P3

(12) United States Plant Patent
Beatson

(10) Patent No.: US PP25,658 P3
(45) Date of Patent: Jun. 30, 2015

(54) HOP PLANT NAMED 'HORT3953'

(50) Latin Name: ***Humulus lupulus* L.**
Varietal Denomination: Hort3953

(71) Applicant: The New Zealand Institute for Plant and Food Research Limited, Auckland (NZ)

(72) Inventor: Ron Beatson, Motueka (NZ)

(73) Assignee: The New Zealand Institute for Plant and Food Research Limited, Auckland (NZ)

( * ) Notice: Subject to any disclaimer, the term of this patent is extended or adjusted under 35 U.S.C. 154(b) by 131 days.

(21) Appl. No.: 13/815,772

(22) Filed: Mar. 15, 2013

(65) Prior Publication Data

US 2014/0090123 P1 Mar. 27, 2014

Related U.S. Application Data

(60) Provisional application No. 61/705,294, filed on Sep. 25, 2012.

(51) Int. Cl.
*A01H 5/08* (2006.01)

(52) U.S. Cl.
USPC ..... Plt./236
CPC ..... *A01H 5/08* (2013.01)

(58) Field of Classification Search
USPC ..... Plt./236
See application file for complete search history.

*Primary Examiner* — Susan McCormick Ewoldt
(74) *Attorney, Agent, or Firm* — Lathrop & Gage LLP

(57) ABSTRACT

A new and distinct hop plant is described. The triploid cultivar results out of selection from a population of seedlings derived from the deliberate crossing the unreleased selections 00-L125-09 (not patented) and 99-58-39 (not patented). The new variety, 'Hort3953', is distinguished from others by its late spring growth and late cone maturity along with a high alpha:beta acids ratio. The new variety is suitable for beer flavouring.

5 Drawing Sheets

Genus and species of plant claimed: *Humulus lupulus* L.
Variety denomination: 'Hort3953'.

BACKGROUND OF THE INVENTION

The new cultivar was selected from a population of triploid seedlings derived from the deliberate crossing of the unreleased selections 00-L125-09 (seed parent) (not patented) and 99-58-39 (pollen parent) (not patented) in March 2004 at Motueka, New Zealand. Triploid seedlings obtained from this cross were grown in a nursery at the same location during the 2004-05 season and subsequently planted in the field. In 2006 'Hort3953' was identified as having potential as a new variety and given the breeder code 04-39-53. This cultivar was selected on the basis of its agronomic performance, seedlessness and chemistry profile.

SUMMARY OF THE INVENTION

A new and distinct hop plant is described. 'Hort3953' is a triploid cultivar, it is distinguished from others by late spring growth and late cone maturity along with a high alpha:beta acids ratio. It is also characterised by large cone size. The new variety is suitable for beer flavouring.

'Hort3953' underwent performance monitoring for agronomic and chemistry traits of commercial importance during 2006/07 and 2007/08. In 2007/08 it was asexually propagated via rhizome cuttings for a small plot replicated trial which was established in the 2008/09 season. The resulting plants were found to be true to type demonstrating that the characteristics of the new variety are stable and transmitted without change through succeeding generations. For four seasons, from 2008/09 to 2011/12, 'Hort3953' was trialled, along with three other promising selections and commercial cultivars 'Pacific Jade' (not patented) and 'Pacific Gem' (not patented), for its commercial potential. In the winter of 2009 it was decided to advance 'Hort3953' to larger-scale testing. Over the next two seasons the new cultivar underwent extensive brewing, agronomic, and chemistry evaluations at Motueka, New Zealand.

'Hort3953' is maintained at Motueka where it has undergone observations for uniformity. All plants have been found to be true to type, that is, no off types have been observed. 'Hort3953' is distinguished from its parental selections, as 'Hort3953' is female, triploid and has a seed content of <2% w/w of the cones while the seed parent, 00-L125-09 is a female, tetraploid and has a seed content of >10% w/w of the cones. The pollen parent, 99-58-39 is a male diploid. Under New Zealand growing conditions 'Hort3953' is distinguished from varieties of common knowledge by the following characteristics:

When grown in Motueka 'Hort3953' has late spring growth and late cone maturity while 'Pacific Jade' has early spring growth and mid season cone maturity. 'Hort3953' cones also have higher alpha acids content compared to those of 'Pacific Jade', along with a higher farnesene content and a higher alpha:beta acids ratio.

'Hort3953' cones also have a higher alpha acids content, farnesene content, and alpha:beta acids ratio when compared with 'Pacific Gem'. When grown in Motueka the spring growth of 'Pacific Gem' is mid season as is the cone maturity whereas the spring growth of 'Hort3953' under the same conditions is late as is the cone maturity.

BRIEF DESCRIPTION OF THE DRAWINGS

The accompanying photographs show typical specimens of the plant habit, cones, and leaves of the new cultivar as depicted in colours as nearly true as is reasonably possible to make the same in colour illustration of this character.

BOTANICAL DESCRIPTION

Figure 1:
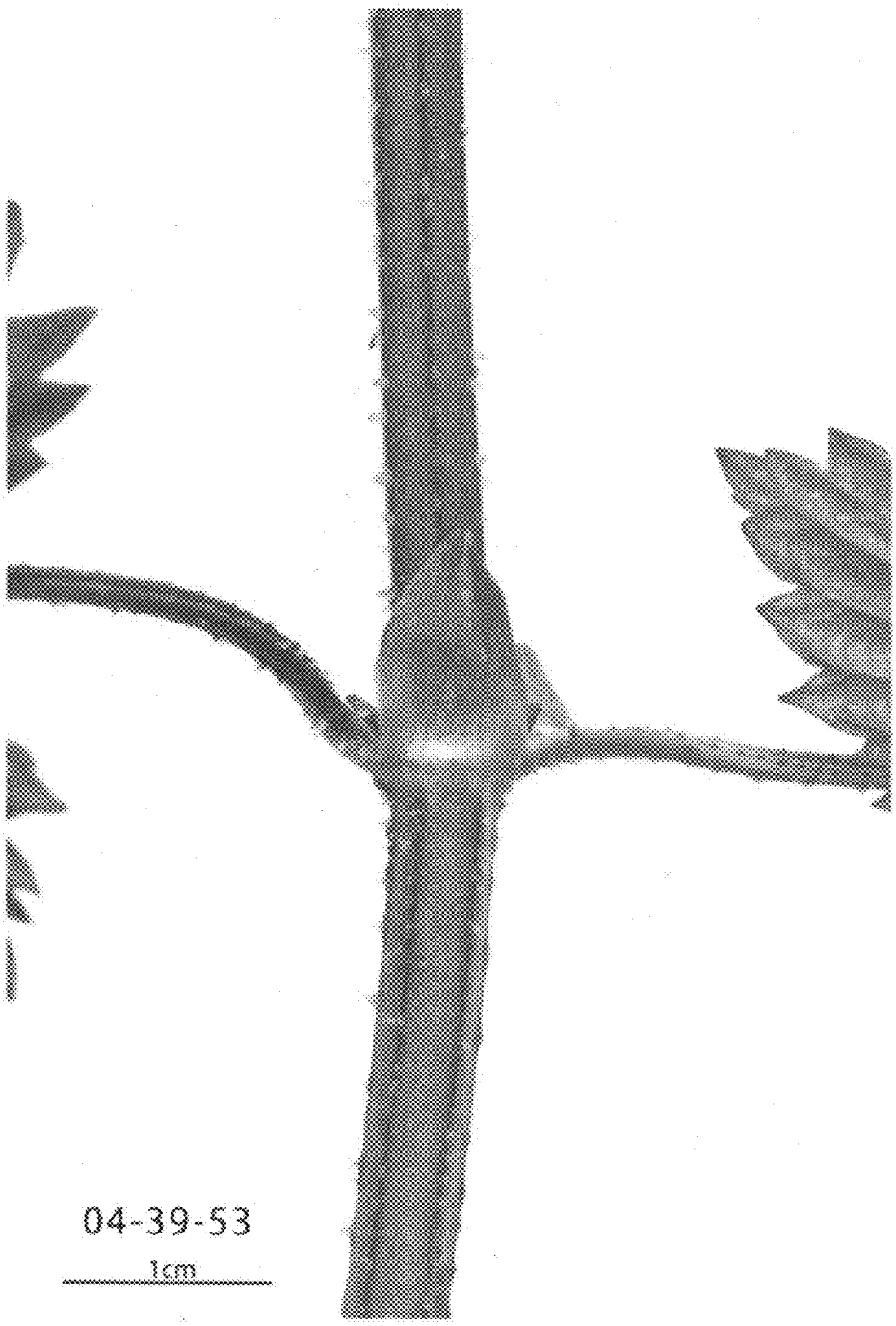
FIG. 1: close up of mature 'Hort3953' vine in the studio.
Figure 2:
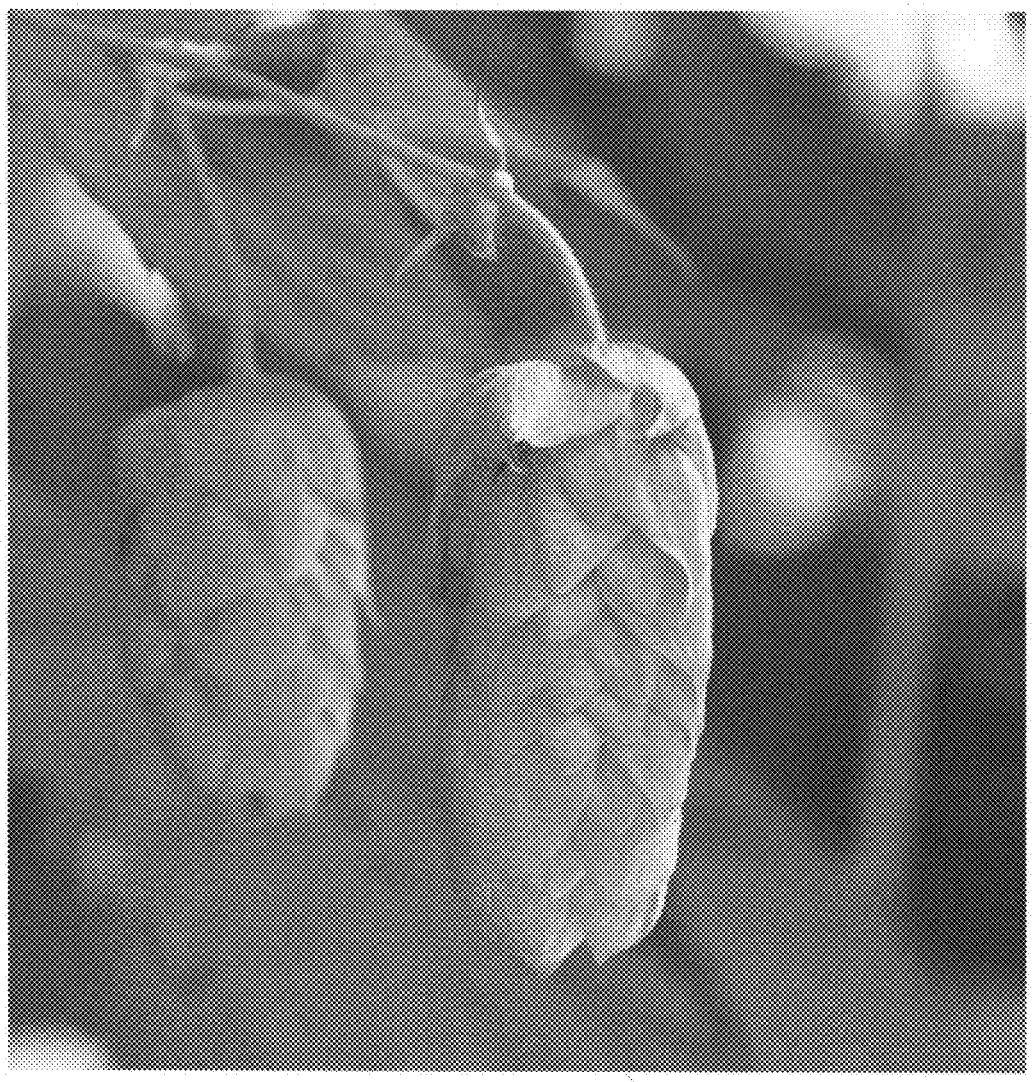
FIG. 2: 'Hort3953' cones in the field.
Figure 3A:
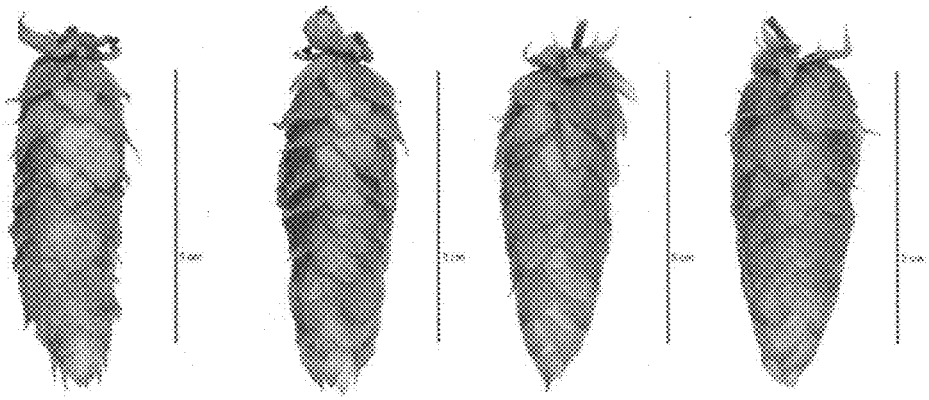
FIG. 3: 'Hort3953' (A), 'Pacific Gem' (B), and 'Pacific Jade' (C) cones.
Figure 3B:
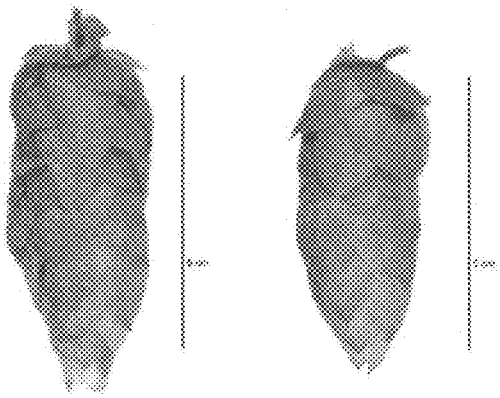
Figure 3C:
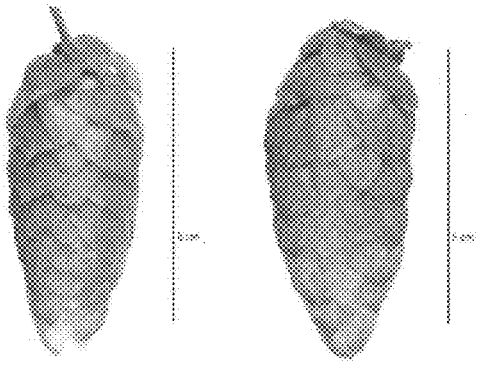
Figure 4A:
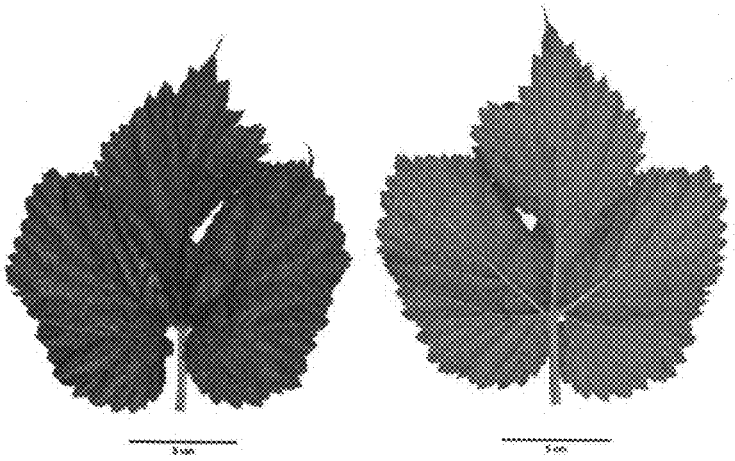
FIG. 4: Upper and underside of 'Hort3953' (A), 'Pacific Gem' (B), and 'Pacific Jade' (C) leaves.
Figure 4B:
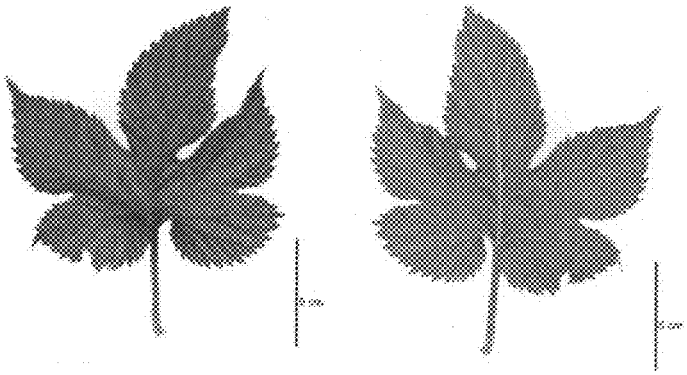
Figure 4C:
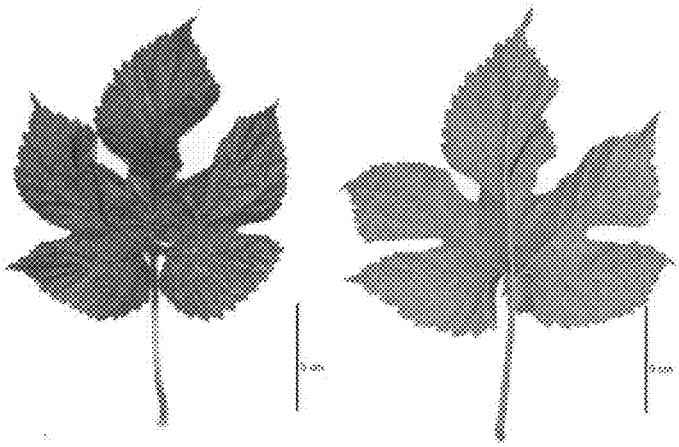

The following is a description of the new cultivar with colour terminology in accordance with The Royal Horticultural Society Colour Charts (R.H.S.C.C.) 2001 edition. The specimens described were grown at Motueka, New Zealand. The observations were made over the 2011-2014 seasons.

Plant form and vigour: Plants are of a normal growth type and produce a high yield (over 2750 kg/ha, four year average) of late maturing cones. The main shoot of a one year old plant was 12.2 mm in diameter with 232 mm long internodes and was yellow-green 144 B in colour. The bine stripe is near yellow-green 144 A with small proportion of weak anthocyanin colouration of near red-purple 59 B.

Laterals: The side shoots from the middle third of the plant were of medium length, an average of approximately 71 cm, and produce a medium number of cones, an average of 37, from approximately 9 nodes. The side shoots from the top third of the plant were longer, 104.3 cm, and produce more cones, an average of 45, from approximately 9 nodes. Whereas 'Pacific Gem' was observed to have longer laterals from the middle third than the top third, an average of 121.8 cm and 94 cm in length respectively, and 'Pacific Jade' was observed to have laterals of a similar average length in both the middle and top third, 77 cm and 68.7 cm respectively.

Leaves: The leaves are strongly lobed with predominantly three lobes, whereas both 'Pacific Gem' and 'Pacific Jade' both have predominantly five lobed leaves. The medium—large weakly blistered leaves are opposite with an auriculate base, acute apex, and broad dentate margins. The upper leaf surface colour is near 134A with veins having near 139C colour. The average leaf size is 170 mm in length and 170 mm in width.

Stipules: Are medium sized and upright with a narrow short acuminate tip.

Cones: Are long and cylindrical to narrow ovate in shape. The open bracts have a right angle to obtuse apex, where the tip is differentiated it is a medium length acuminate tip. Harvest is late in the New Zealand season, commencing mid to late March, under normal conditions. The cones average length is 50 mm with an average cone green weight of 1500 mg and an average dry weight of 300 mg. The dried cone bracts are near 144A in colour and the bracteoles near 144D.

Figure 5:
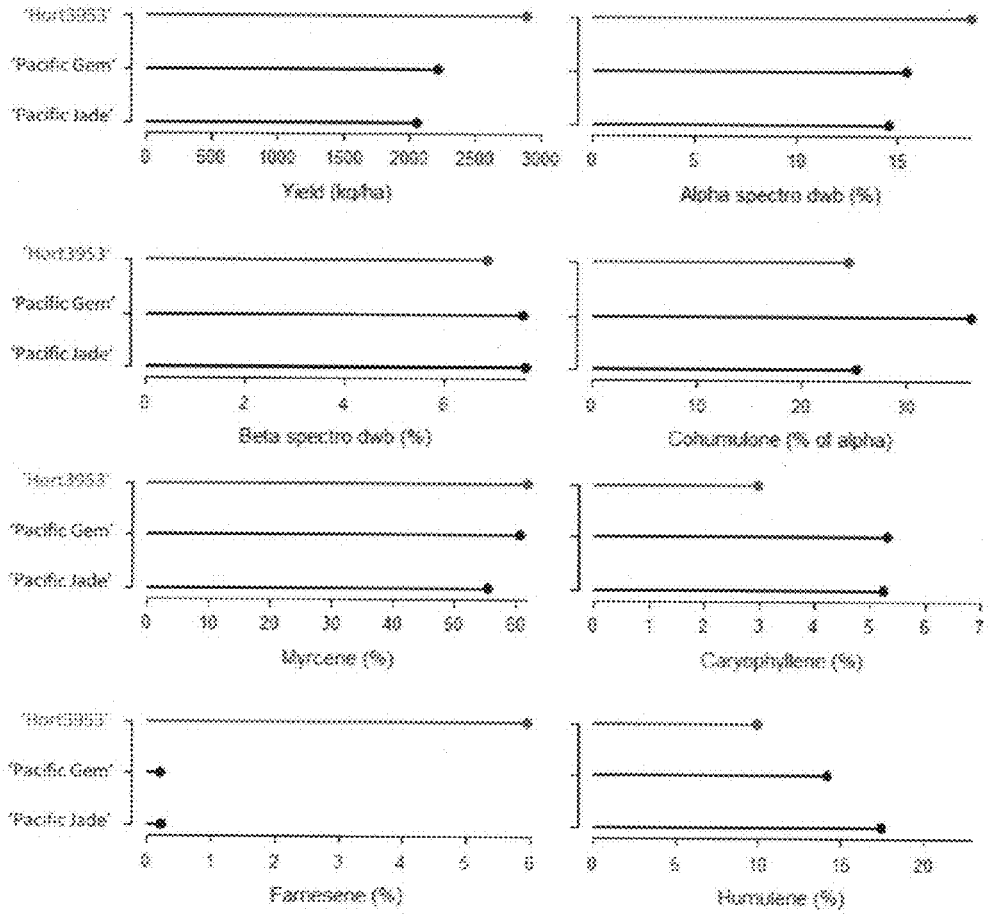
FIG. 5 shows the four year mean of at harvest chemistry profiles for 'Hort3953' and two comparator cultivars 'Pacific Gem' and 'Pacific Jade'. Trials and testing were conducted in Motueka, New Zealand.

Chemistry profile: 'Hort3953' has undergone extensive chemistry profile testing, FIG. 5 shows averages of four years data. The data provided compares 'Hort3953' with 'Pacific Gem' and 'Pacific Jade' as these are commonly grown alpha hop cultivars in New Zealand. The chemistry profile of 'Hort3953' differs significantly from both 'Pacific Gem' and 'Pacific Jade' in a number of ways; these include a higher percentage of alpha acids and slightly lower percentage of beta acids than either comparator. 'Hort3953' has a similar cohumulone percentage to 'Pacific Jade', both of which are considerably lower than that of 'Pacific Gem'. 'Hort3953' has an average of 6% farnesene while both comparators have around 0.2% whereas both comparators have higher caryophyllene and humulene percentages.

Use: Primarily flavouring and bittering ingredient for beer.

Pest and disease: 'Hort3953' does not appear particularly resistant or susceptible to any particular pests or diseases known to afflict *Humulus lupulus.*

Hardiness: The plant cold hardiness according to the American zone classification has not been determined.

The invention claimed is:

1. A new and distinct hop plant substantially as described and illustrated herein.

* * * * *